United States Patent [19]

Toda

[11] Patent Number: 4,962,274
[45] Date of Patent: Oct. 9, 1990

[54] PROCESS FOR SEPARATING ALKYL-SUBSTITUTED NAPHTHALENE DERIVATIVES USING CLATHRATE COMPLEXES

[75] Inventor: Fumio Toda, Shigenobu, Japan

[73] Assignee: Kureha Kagaku Kogyo K.K., Tokyo, Japan

[21] Appl. No.: 403,961

[22] Filed: Sep. 7, 1989

[30] Foreign Application Priority Data

Sep. 10, 1988 [JP] Japan .................................. 63-225540
Sep. 10, 1988 [JP] Japan .................................. 63-225541
Feb. 15, 1989 [JP] Japan .................................... 1-33674

[51] Int. Cl.$^5$ ............................................. C07C 7/152
[52] U.S. Cl. ................................. 585/833; 585/864; 585/867
[58] Field of Search ............... 585/833, 804, 863, 864, 585/867

[56] References Cited

U.S. PATENT DOCUMENTS

| | | | |
|---|---|---|---|
| 3,670,039 | 6/1972 | Davis | 585/865 |
| 3,870,745 | 3/1975 | Angstadt | 585/471 |
| 3,936,509 | 2/1976 | Nagahama et al. | 585/865 |

FOREIGN PATENT DOCUMENTS

| | | |
|---|---|---|
| 69055 | 6/1975 | Japan . |
| 70347 | 6/1975 | Japan . |
| 23406 | 5/1981 | Japan . |
| 15923 | 6/1982 | Japan . |
| 153233 | 7/1987 | Japan . |
| 88141 | 4/1988 | Japan . |

*Primary Examiner*—Glenn Caldarola
*Assistant Examiner*—William C. Diemler
*Attorney, Agent, or Firm*—Lowe, Price, LeBlanc, Becker & Shur

[57] ABSTRACT

A process for the separation of an alkyl-substituted naphthalene from a mixture containing the desired alkyl-substituted naphthalene and at least one isomer thereof comprises placing 9,9'-bianthracene in contact with the mixture to form a clathrate complex of the formula

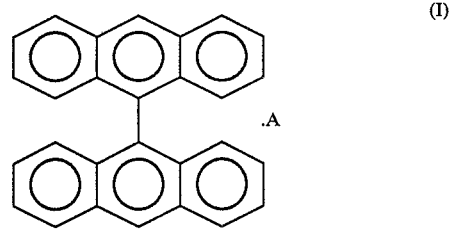

(I)

wherein A represents 2-methylnaphthalene, 2-isopropyl-naphthalene of 2,6-diisopropylnaphthalene, collecting the clathrate complex by filtration, subjecting the clathrate complex to thermal decomposition, and then recovering the alkyl-substituted naphthalene derivative.

4 Claims, 3 Drawing Sheets

PROCESS FOR SEPARATING ALKYL-SUBSTITUTED NAPHTHALENE DERIVATIVES USING CLATHRATE COMPLEXES

FIELD OF THE INVENTION

This invention relates to novel clathrate complexes and also to a process for separating 2-methylnaphthalene (hereinafter abbreviated as "2-MN"), 2-isopropylnaphthalene (hereinafter abbreviated as "2-IPN") or 2,6-diisopropylnaphthalene (hereinafter abbreviated as "2,6-DIPN") from a mixture of the desired alkyl-substituted naphthalene derivative and at least one isomer thereof by using one of the corresponding clathrate complexes.

BACKGROUND OF THE INVENTION

2-MN is known as a raw material for vitamin $K_3$ and the like. It is also useful as a raw material for 2,6-naphthalenedicarboxylic acid, a monomer for high performance polyester resins whose development is under progress in recent years. 2-MN is contained in naphthalene oil, obtained from coal tar, and also in heavy oil, available upon cracking of petroleum. 2-MN is concentrated by distillation out of mixtures consisting of itself and co-existing components such as 1-MN, biphenyl and acenaphthene. Of these co-existing components, separation of 2-MN from 1-MN is particularly difficult.

In addition, 2-IPN is a compound useful as a raw material for $\beta$-naphthol and the like. As raw materials for the production of 2-IPN, IPN mixtures are well-known. IPN mixtures can be produced industrially by using naphthalene and propylene as raw materials to conduct operations including alkylation, transalkylation and distillation.

Furthermore, 2,6-DIPN is a compound useful as a raw material for 2,6-naphthalenedicarboxylic acid, 2,6-dihydroxynaphthalene and 6-hydroxy-2-naphthoic acid, all known as monomers for high performance polyester resins. As raw materials for the production of 2,6-DIPN, DIPN mixtures are well-known. DIPN mixtures are produced industrially by using naphthalene and propylene as raw materials to conduct operations including alkylation, transalkylation and distillation. DIPN mixtures are used in such applications as microencapsulation solvents for carbonless copying paper and electrical insulation oils.

To obtain 2-MN, 2-IPN or 2,6-DIPN from a corresponding mixture of alkyl-substituted naphthalene isomers as described above, it has heretofore been known to use the following methods by way of example.

Namely, proposed methods for the separation and recovery of high-purity 2-MN include a method of combined distillation and crystallization (Japanese Patent Application Laid-Open No. 95923/1982), a method using an adsorbent (Japanese Patent Application Laid-Open No. 88432/1984) and a method involving distillation subsequent to the addition of an alkanolamine (Japanese Patent Application Laid-Open No. 153233/1987).

However, the above methods were all developed by improving efficiencies of methods whose principles had been known. Their application for the separation of isomers having extremely close physical and chemical properties, such as 1-MN and 2-MN, inevitably leads to the need for large and complex facilities, so that an economical disadvantage is unavoidable. Regarding the separation of 2-MN and 1-MN, there has hence been a demand for the development of a novel method which is more advantageous than the conventional separation methods.

In addition, as methods for separating 2-IPN from an IPN mixture, there have been known a method of melt crystallization disclosed in Japanese Patent Application Laid-Open No. 70347/1975 and a method of cooling and crystallization in a lower alcohol solvent disclosed in Japanese Patent Publication No. 23406/1981.

However, the above conventional methods both require crystallization at a temperature as low as $-30°$ C. Therefore, they require not only a powerful cooling apparatus but also a high utility cost. They are hence not suitable for industrial practice. In addition, 2-IPN tends to form fine crystals. This leads to another problem that extreme difficulties are encountered when attempting to obtain 2-IPN in uniform crystals large enough to permit filtration and washing. It is therefore necessary to pay special attention to the conduction of heat and stirring within a crystallization vessel and the scraping of the crystals deposited on the vessel walls. This leads to a further problem that an exclusively-designed crystallization vessel is needed.

Furthermore, as a method for separating 2,6-DIPN from a DIPN mixture, it has been known to obtain high-purity 2,6-DIPN by cooling the DIPN mixture to crystallize 2,6-DIPN and then collecting the resultant crystals by filtration as disclosed in Japanese Patent Application Laid-Open No. 69055/1975. In addition, Japanese Patent Application Laid-Open No. 88141/1988 discloses the separation of 2,6-DIPN from an isopropyl-naphthalene mixture containing both 2,7-DIPN and 2,6-DIPN by using the formation of an adduct between 2,6-DIPN and thiourea.

However, any attempt at industrially practicing the cooling method of an oily DIPN mixture in the process disclosed in Japanese Patent Application Laid-Open No. 69055/1975 requires cooling of the mixture to a temperature below zero. This cooling therefore requires high initial and utility costs. Moreover, it is necessary to make crystals have a uniform and appropriate size in order to facilitate their filtration and washing. This requires delicate and minute adjustments with respect to the conduction of heat and stirring within a crystallization vessel and the scraping of crystals deposited on the vessel walls. This leads to another problem that an exclusively-designed crystallization vessel is needed. Moreover, to obtain 2,6-DIPN having a purity as high as 99% or higher, it is indispensable to combine plural steps of operations for crystallization into a complex process. Accordingly, an economical disadvantage is inevitable.

On the other hand, the method disclosed in Japanese Patent Application Laid-Open No. 88141/1988 takes a long time for the formation of the adduct. Nevertheless, the purity of 2,6-DIPN to be obtained is lower than 98%. It is therefore not fully satisfactory as an industrial method for the production of 2,6-DIPN which is required to have a high level of purity as a monomer source.

SUMMARY OF THE INVENTION

The present invention has been completed in view of the above-described circumstances of the prior art.

An object of this invention is therefore to provide a process for separating a desired alkyl-substituted naphthalene derivative from a mixture of the desired alkyl-substituted naphthalene derivative and at least one isomer thereof and also to provide a clathrate complex useful in the practice of the process.

Another object of this invention is to provide a process for separating 2-MN, permitting separation of high-purity 2-MN out of an MN mixture in simple operations.

A further object of this invention is to provide a process for separating 2-IPN, permitting separation of 2-IPN out of an IPN mixture in simple operations with no need of cooling.

A still further object of this invention is to provide a process for separating 2,6-DIPN, permitting separation of high-purity 2,6-DIPN out of a DIPN mixture in simple operations with no need of cooling.

MEANS FOR THE SOLUTION OF THE PROBLEMS

The present inventor has conducted an extensive investigation under the assumption that an industrially significant separation process may be provided, if a compound could preferentially form a clathrate complex with 2-MN, 2-IPN or 2,6-DIPN when brought into contact with an MN, IPN or DIPN mixture respectively, under conditions requiring no cooling, and if said clathrate complex could decompose into said compound and 2-MN, 2-IPN or 2,6-DIPN in simple operations in such an effective manner that it could be possible to easily recover 2-MN, 2-IPN or 2,6-DIPN of 99% or higher purity from an MN mixture, IPN mixture or DIPN mixture by a series of steps comprising the formation of the clathrate and its decomposition.

As a result, it has been found that 9,9'-bianthracene preferentially forms a clathrate complex with 2-MN, 2-IPN or 2,6-DIPN at room temperature when brought into contact with an MN, IPN or DIPN mixture; respectively. The term "bianthracene" will hereinafter be abbreviated as "BA" for brevity. It has also been found that when heated, the clathrate complex between 9,9'-BA and 2-MN, 2-IPN or 2,6-DIPN is easily decomposed into 2-MN, 2-IPN or 2,6-DIPN and 9,9'-BN and the purity of 2-MN, 2-IPN or 2,6-DIPN thus recovered is improved and is, in many cases, as high as 99% or even higher. These findings have led to the completion of this invention.

The clathrate complex according to this invention consists of 9,9'-BA and an alkyl-substituted naphthalene derivative and is represented by the following formula (I):

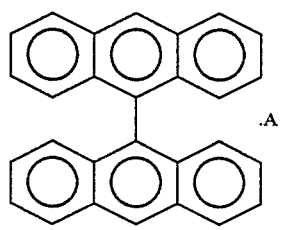

wherein A represents 2-methylnaphthalene, 2-isopropylnaphthalene or 2,6-diisopropylnaphthalene.

Described specifically, the following compounds are mentioned as clathrate complexes according to this invention:

Clathrate complex consisting of 9,9'-BA and 2-MN and represented by the following formula (II):

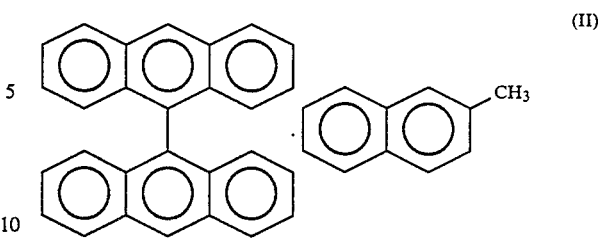

Clathrate complex consisting of 9,9'-BA and 2-IPN and represented by the following formula (III):

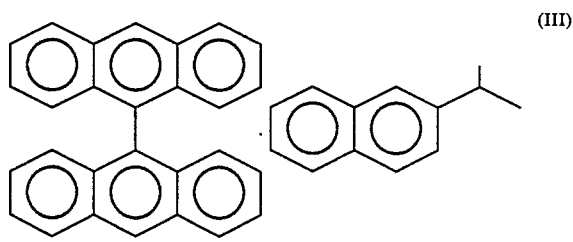

Clathrate complex consisting of 9,9'-BA and 2,6-DIPN and represented by the following formula (IV):

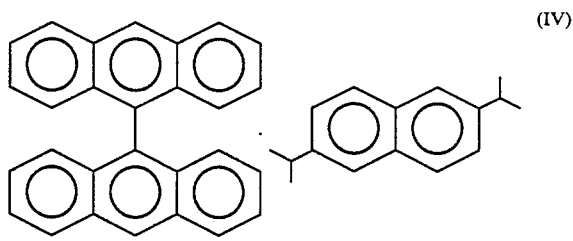

The process according to this invention for the separation of an alkyl-substituted naphthalene derivative selected from 2-MN, 2-IPN and 2,6 DIPN features that upon separation of 2-MN, 2-IPN or 2,6-DIPN from a mixture containing 2MN, 2-IPN or 2,6-DIPN and at least one isomer thereof, 9,9'-BA is brought into contact with the mixture to form a clathrate complex represented by the following formula (I):

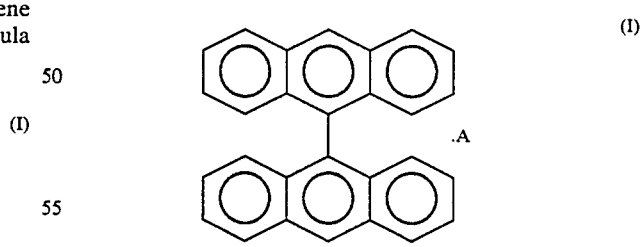

wherein A represents the alkyl-substituted naphthalene derivative, the clathrate complex is separated by filtration and is subjected to thermal decomposition, and the alkyl-substituted naphthalene derivative is then recovered.

DETAILED DESCRIPTION OF PREFERRED EMBODIMENTS

Figure 1:
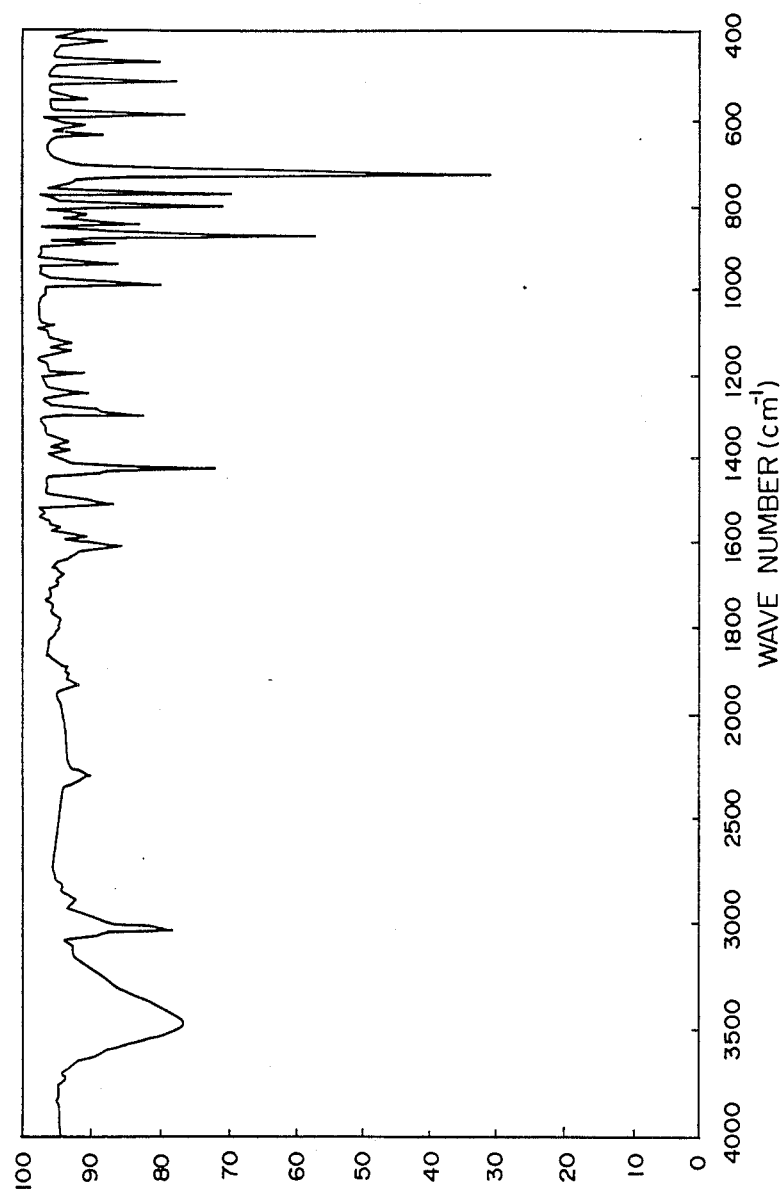
FIG. 1 diagrammatically illustrates an infrared absorption spectrum of the clathrate complex according to this invention, which is represented by the formula (II)

Among the clathrate complexes according to this invention, the clathrate complex represented by the formula (II) is a crystalline substance of a pale yellow color, which shows the infrared absorption spectrum of FIG. 1 when analyzed with the KBr method. When heated, it decomposes into 9,9'-BA and 2-MN.

Figure 2:
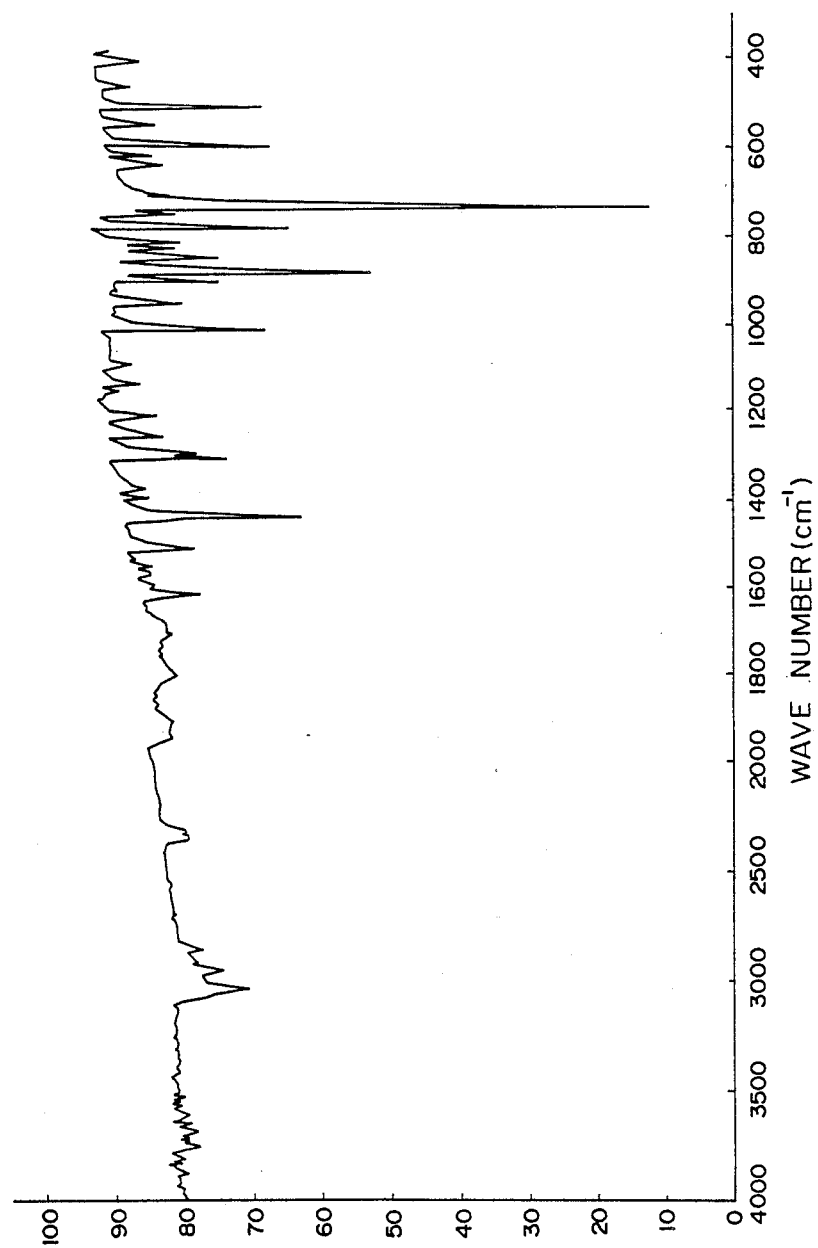
FIG. 2 diagrammatically shows an infrared absorption spectrum of the clathrate complex according to this invention, which is represented by the formula (III)

The clathrate complex represented by the formula (III) is a colorless crystalline substance, which shows the infrared absorption spectrum of FIG. 2 when analyzed with the KBr method. When heated, it decomposes into 9,9'-BA and 2-IPN.

Figure 3:
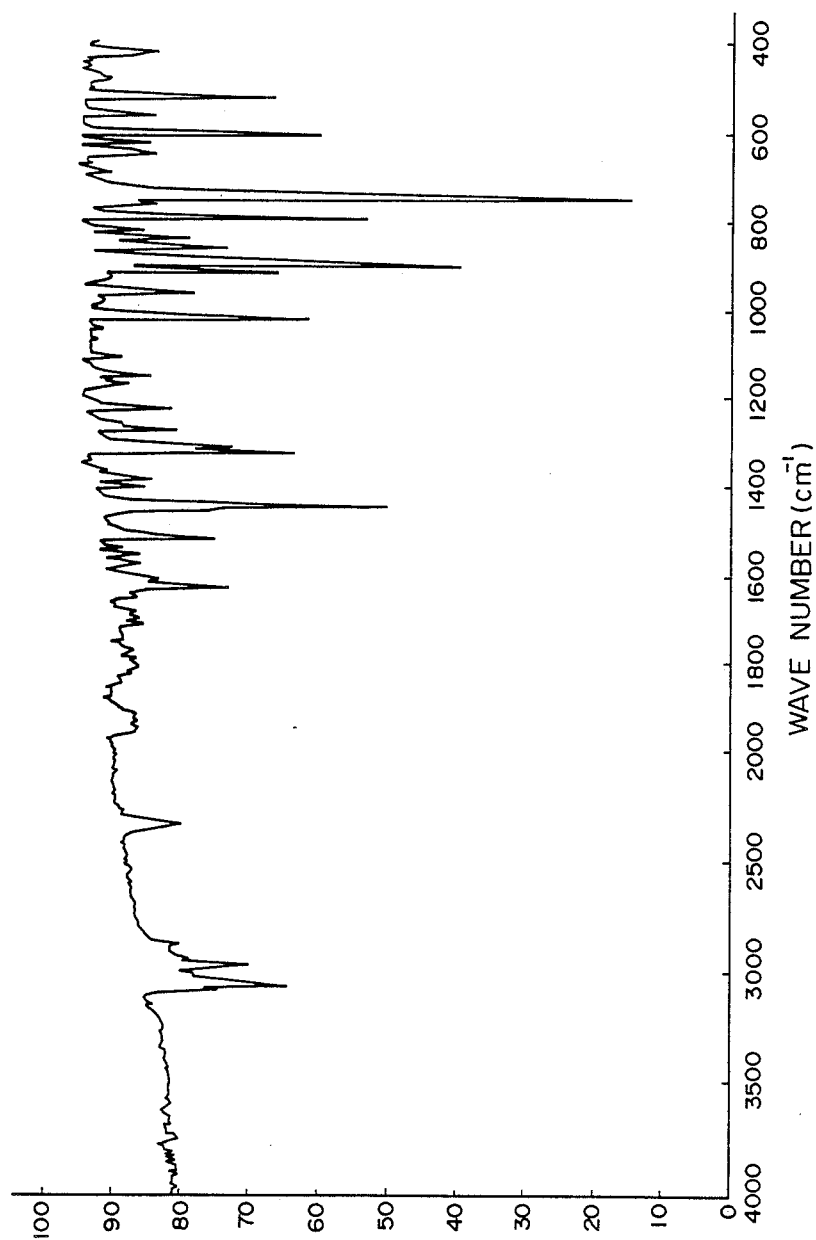
FIG. 3 diagrammatically depicts an infrared absorption spectrum of the clathrate complex according to this invention, which is represented by the formula (IV)

In addition, the clathrate complex represented by the formula (IV) is a colorless crystalline substance, which shows the infrared absorption spectrum of FIG. 3 when analyzed with the KBr method. When heated, it decomposes into 9,9'-BA and 2,6-DIPN.

Each clathrate complex (I) of this invention can be easily formed by bringing 9,9'-BA into contact at room temperature with a mixture containing the corresponding alkyl-substituted naphthalene derivative selected from 2-MN, 2-IPN or 2,6-DIPN and at least one isomer thereof. Since 9,9'-BA preferentially forms the clathrate complex with 2-MN, 2-IPN or 2,6-DIPN; respectively, at room temperature and the clathrate complex thus formed decomposes into 9,9'-BA and 2-MN, 2-IPN or 2,6-DIPN when heated, the use of the formation of the clathrate complex and its decomposition in accordance with the present invention makes it possible to easily separate 2-MN, 2-IPN or 2,6-DIPN from the corresponding mixture.

The separation process according to this invention will next be described in detail.

As the alkyl-substituted naphthalene derivative mixture usable as a raw material in the process of this invention, an MN mixture, IPN mixture or DIPN mixture can be employed.

An MN mixture is obtained by distillation of a naphthalene oil obtained from coal tar or of a heavy oil available upon cracking of petroleum, and contains 1-MN and 2-MN as principal components.

An IPN mixture is obtained by subjecting naphthalene and propylene to alkylation and transalkylation in the presence of a solid acid catalyst such as silica-alumina or a synthetic zeolite and then distilling propylated naphthalenes thus formed. Its principal components are 2-IPN and 1-IPN. The content of 2-IPN in the IPN mixture varies depending on the operational conditions employed for the alkylation, transalkylation and distillation but may usually range from 50 wt.% to 95 wt.%.

A DIPN mixture is obtained by subjecting naphthalene and propylene to alkylation and transalkylation in the presence of a solid acid catalyst such as silica-alumina or a synthetic zeolite and then distilling propylated naphthalenes thus formed. Its principal components are 2,6-DIPN and 2,7-DIPN. As minor components, other DIPN isomers account for a large majority of the minor components. The content of 2,6-DIPN in the DIPN mixture varies depending on the operational conditions employed for the alkylation, transalkylation and distillation but may usually range from 15 wt.% to 50 wt.%.

9,9'-BA which is essential in the practice of the process of this invention has a form of pale yellow crystals having a melting point of 314° C. It can be easily obtained by further reduction of 9-anthrone formed by reducing anthraquinone. Thus, 9,9'-BA is a raw material suitable for industrial use.

To form the above clathrate complex by using a mixture, which contains the corresponding alkyl-substituted naphthalene derivative and at least one isomer thereof and is in a liquid form, and 9,9'-BA, it is only necessary to mix crystalline 9,9'-BA with the liquid mixture either as is or after dissolving or suspending it in a liquid medium. No particular limitation is imposed on the concentration of the alkyl-substituted naphthalene derivative, namely, 2-MN, 2 IPN or 2,6-DIPN in the mixture. Although it is not essential to use a liquid medium, a liquid medium may be used so long as its use can bring about any advantage in operations.

9,9'-BA may be used at a molar ratio of 0.2-2 times, preferably 0.5-1.2 times relative to the amount of 2-MN, 1-IPN or 2,6-DIPN contained in the mixture. If 9,9'-BA is used in any amount smaller than the lower limit of the range, the recovery rate of 2-MN, 1-IPN or 2,6-DIPN is lowered. If 9,9'-BA is used in any amount greater than the upper limit of the range, the effective utilization of 9,9'-BA is reduced, and moreover, 9,9'-BA form clathrate complexes with one or more components other than 2-MN, 2-IPN or 2,6-DIPN and 2-MN, 2-IPN or 2,6-DIPN is recovered with a reduced purity. It is therefore not practical to add 9,9'-BA in any amount outside the range.

In the process of this invention, the temperature suitable for the formation of the clathrate complex between 9,9'-BA and 2-MN, 2-IPN or 2,6-DIPN may be from 5° C. to 50° C., preferably from 10° C. to 35° C.

When forming the clathrate complex, it is preferable to stir the mixture which has been obtained by adding 9,9'-BA to the alkyl-substituted naphthalene mixture. This stirring is however not essential. Unlike the so-called melt crystallization in which an IPN mixture or DIPN mixture is cooled to crystallize 2-IPN or 2,6-DIPN and the resulting crystals are then collected by filtration, no delicate control of temperature and stirring conditions is needed.

The time required for the formation of the clathrate complex is generally not longer than 8 hours. The clathrate complex of 9,9'-BA and 2-MN, 2-IPN or 2,6-DIPN has a low solubility in a liquid solvent such as hexane or acetone. Even if no particular attention is paid upon stirring, the complex therefore precipitates as crystals of shape and size permitting easy filtration and washing.

After formation of the clathrate complex in the manner described above, the clathrate complex and unclathrated 9,9'-BA are separated from the rest by conventional filtration. In order to avoid a purity loss due to the liquid alkyl-substituted naphthalene mixture accompanying to the clathrate complex, it is preferable to wash the clathrate complex with a small amount of a solvent. As such a solvent, petroleum ether, hexane, toluene, acetone or the like is suited.

The clathrate complex separated as described above decomposes into 9,9'-BA and 2-MN, 2-IPN or 2,6-DIPN when heated.

In the case of the clathrate complex represented by the formula (II), it decomposes into 9,9'-BA and 2-MN when heated, so that an MN mixture with 2-MN concentrated therein can be distilled out. Although the heating temperature varies depending on the pressure, it is necessary to heat it to a temperature of 120° C. or higher, preferably to from 120° C. to 200° C. under normal pressure. It is also possible to concentrate 2-MN by separating 9,9'-BA and 2-MN from each other by a method such as extraction. Extraction allows to obtain 2-MN at a lower temperature than the separation by heating. As exemplary extraction solvents, hexane, acetone, toluene and the like can be mentioned. 2-MN having a purity of at least 99% can be obtained by repeating the above operations as needed.

In the case of the clathrate complex represented by the formula (III) or (IV), it decomposes into 9,9'-BA and 2-IPN or 2,6-DIPN whose purity is at least 99%. The heating temperature varies depending on the pressure. In the case of the clathrate complex represented by the formula (III) for example, the clathrate complex is heated to 120° C. or higher, preferably to 120-200° C. under normal pressure. In the case of the clathrate complex represented by the formula (IV), it is heated to 165° C. or higher, preferably to 165-250° C. Since the melting points of 2-IPN, 2,6-DIPN and 9,9'-BA are 15° C., 69° C. and 314° C. respectively, the decomposition product obtained by the heating is in the form of a mixture of solid 9,9'-BA and liquid 2-IPN or 2,6-DIPN. Separation of 2-IPN or 2,6-DIPN from the mixture by distillation, extraction or the like gives 2-IPN or 2,6-DIPN whose purity is at least 99%.

ADVANTAGES OF THE INVENTION

The clathrate complexes of this invention can be formed easily at room temperature and can also be decomposed easily. According to the process of this invention, it is therefore possible to recover an alkyl-substituted naphthalene derivative selected from 2-MN, 2-IPN or 2,6-DIPN and having a purity of at least 99% from a mixture, which contains the desired alkyl-substituted naphthalene derivative and at least one isomer thereof, by using the formation and decomposition of the corresponding clathrate without need for a complex crystallization tank equipped with a cooling apparatus.

2-MN, 2-IPN and 2,6-DIPN separated by the process of this invention are useful compounds. Namely, 2-MN is used as a raw material for vitamin $K_3$ and the like. In addition, it may be oxidized into 2-naphthoic acid, which may then converted into the potassium salt. By heating the potassium salt in the presence of carbon dioxide under elevated pressure, naphthalene and dipotassium 2,6-naphthalenedicarboxylate are formed. Thereafter, the potassium salt may be converted into 2,6-naphthalenedicarboxylic acid. Furthermore, after subjecting 2-MN to alkylation, formylation or acylation, the resulting 2,6-isomer is separated and then oxidized by a suitable method. This also makes it possible to convert 2-MN into 2,6naphthalenedicarboxylic acid useful as a monomer for high performance polyester resins. In addition, 2-IPN is a compound useful as a raw material for β-naphthol or the like. Further, 2,6-DIPN is a compound useful as a raw material for 2,6-naphthalenedicarboxylic acid, 2,6-dihydroxynaphthalene and 6-hydroxy-2-naphthoic acid which are all monomers for high performance polyester resins.

The process of this invention will hereinafter be described in the following examples. It should however be borne in mind that the process of this invention is not limited by the following examples.

EXAMPLES

Example 1

2.84 g of an MN mixture containing 45% (9.0 mmol) of 2-MN and 3.55 g (10.0 mmol) of 9,9'-BA were suspended in 5 ml of hexane, followed by stirring at room temperature for 4 hours. A solid precipitate was collected by filtration, washed with a small amount of hexane and then dried in the air, thereby obtaining 4.66 g of a solid matter which contained a clathrate complex of 9,9'-BA and 2-MN. When the solid matter was heated to about 200° C. under reduced pressure (25 mmHg), 1.4 g of an MN mixture were distilled out. The content of 2-MN in the mixture was 86.5%. The recovery rate of -MN was hence 76.9%.

Example 2

1.73 g of an MN mixture containing 82% (10.0 mmol) of 2-MN and 3.54 g (10.0 mmol) of 9,9'-BA were suspended in 5 ml of hexane, followed by stirring at room temperature for 4 hours. A solid precipitate was collected by filtration, washed with a small amount of hexane and then dried in the air, thereby obtaining 4.62 g of a solid matter which contained a clathrate complex of 9,9'-BA and 2-MN. When the solid matter was heated to about 200° C. under reduced pressure (25 mmHg), 1.09 g of an MN mixture were distilled out. The content of 2-MN in the mixture was 99.1%. The recovery rate of 2-MN was hence 76.0%.

Example 3

A suspension of 3.0 g (8.47 mmol) of 9,9'-BA in 5 ml of acetone was mixed with 1.59 g of an IPN mixture containing 90% (8.40 mmol) of 2-IPN, followed by stirring at room temperature for 3 hours. Colorless prismatic crystals thus formed were collected by filtration, washed with a small amount of acetone and then dried in the air, thereby obtaining 3.27 g (6.23 mmol) of a 1:1 clathrate complex of 9,9'-BA and 2-IPN. When the clathrate complex was subjected to thermogravimetric analysis (TGA) at a heating rate of 10° C./min in a nitrogen gas stream of normal pressure, weight reduction was observed in a temperature range of from 100° C. to 178° C.

When crystals of the clathrate complex were heated to about 200° C. under reduced pressure (25 mmHg), 1.05 g of 2-IPN were distilled out. Its recovery rate was 73.4% based on the content of 2-IPN in the IPN mixture as the raw material. Its purity was found to be 99.9% by DSC.

Example 4

1.06 g of an IPN mixture containing 90% (5.60 mmol) of 2-IPN and 2.0 g (5.64 mmol) of 9,9'-BA were mixed. The resultant mixture was left over for 6 hours at room temperature. Crystals thus formed were collected by filtration, washed with a small amount of hexane and then dried in the air, thereby obtaining 2.88 g of a 1:1 clathrate complex of 9,9'-BA and 2-IPN. When crystals of the clathrate complex were heated to about 200° C. under reduced pressure (25 mmHg), 0.70 g of 2-IPN were distilled out. Recovery rate: 73.4%. Purity: 99.9%.

Example 5

5.3 g of a DIPN containing 40% (10.0 mmol) of 2,6-DIPN and 3.54 g (10.0 mmol) of 9,9'-BA were suspended in 5 ml of acetone, followed by stirring for 3 hours at room temperature Colorless prismatic crystals thus formed were collected by filtration, washed with a small amount of acetone and then dried in the air, thereby obtaining 4.45 (7.86 mmol) of a 1:1 clathrate complex of 9,9'-BA and 2,6-DIPN. When the clathrate complex was subjected to thermogravimetric analysis (TGA) at a heating rate of 10° C./min in a nitrogen gas stream of normal pressure, weight reduction was observed in a temperature range of from 140° C. to 204° C.

When crystals of the clathrate complex were heated to about 200° C. under reduced pressure (25 mmHg), 1.67 g of 2,6-DIPN were distilled out. Its recovery rate was 78.6% based on the content of 2,6-DIPN in the DIPN mixture as the raw material. Its purity was found to be 99.8% by DSC.

Example 6

6.0 g of a DIPN mixture containing 20% (5.65 mmol) of 2,6-DIPN and 2.0 g (5.64 mmol) of 9,9'-BA were mixed. The resultant mixture was left over for 6 hours at room temperature. Crystals thus formed were collected by filtration, washed with a small amount of hexane and then dried in the air, thereby obtaining 2.35 g of a 1:1 clathrate complex of 9,9'-BA and 2,6-DIPN. When crystals of the clathrate complex were heated to about 200° C. under reduced pressure (25 mmHg), 0.80 g of 2,6-DIPN (3.77 mmol) were distilled out. Recovery rate: 73.4%. Purity: 99.9%.

What is claimed is:

1. A process for the separation of an alkyl-substituted naphthalene derivative selected from the group consisting of 2-methylnaphthalene, 2-isopropylnaphthalene and 2,6-diisopropylnaphthalene from a mixture containing the desired alkyl-substituted naphthalene derivative and at least one isomer thereof, which comprises:

bringing 9,9'-bianthracene into contact with the mixture to form a clathrate complex represented by the following formula (I):

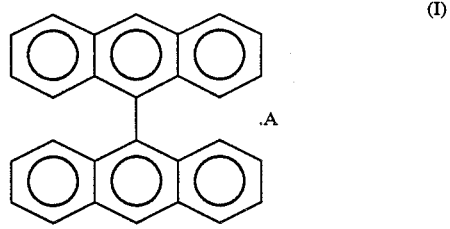

(I)

wherein A represents the alkyl-substituted naphthalene derivative;
    collecting the clathrate complex by filtration; subjecting the clathrate complex to thermal decomposition; and
    recovering the alkyl-substituted naphthalene derivative.

2. The method as claimed in claim 1, wherein the alkyl-substituted naphthalene derivative is 2-methylnaphthalene.

3. The method as claimed in claim 1, wherein the alkyl-substituted naphthalene derivative is 2-isopropylnaphthalene.

4. The method as claimed in claim 1, wherein the alkyl-substituted naphthalene derivative is 2,6diisopropylnaphthalene.

* * * * *